United States Patent [19]

Cherksey

[11] Patent Number: 5,516,516
[45] Date of Patent: May 14, 1996

[54] METHOD OF PREPARING MUIRA PUAMA EXTRACT AND ITS USE FOR DECREASING BODY FAT PERCENTAGE AND INCREASING LEAN MUSCLE MASS

[76] Inventor: Bruce D. Cherksey, 608 Garden St., Hoboken, N.J. 07030

[21] Appl. No.: 247,906

[22] Filed: May 23, 1994

Related U.S. Application Data

[63] Continuation-in-part of Ser. No. 139,512, Oct. 19, 1993, abandoned.

[51] Int. Cl.$^6$ ................................................... A61K 35/78
[52] U.S. Cl. ........................................ 424/195.1; 514/909
[58] Field of Search .......................... 424/195.1; 514/909

[56] References Cited

PUBLICATIONS

Miller, R, A, "The Magical and Ritual Use of Aphrodisiacs", Dasting Books, Roc. Ver. 1985.

*Primary Examiner*—John W. Rollins
*Attorney, Agent, or Firm*—Lyon & Lyon

[57] ABSTRACT

A method, and related compositions, for reducing body fat percentage, increasing lean muscle mass and/or lowering cholesterol levels in individuals. The method consists of the ingestion of an extract derived from muira puama root, bark or other wood material. A method of preparing the muira puama extract into an easily ingestible and manipulatable solid form, and pharmaceutical compositions for use by mammalian subjects, are also disclosed.

18 Claims, No Drawings

METHOD OF PREPARING MUIRA PUAMA EXTRACT AND ITS USE FOR DECREASING BODY FAT PERCENTAGE AND INCREASING LEAN MUSCLE MASS

RELATED APPLICATIONS

This application is a continuation-in-part of U.S. patent application Ser. No. 08/139,512, filed Oct. 19, 1993 now abandoned. The entire disclosure of that application is incorporated by reference herein.

FIELD OF THE INVENTION

This invention relates to compositions derived from muira puama and their use for reducing body fat and/or increasing lean muscle mass.

BACKGROUND OF THE INVENTION

Muira puama is the wood derived from *Liriosma ovata* Miers, Oleaceae, also known as *Acanthea virilis* Wehmer, Acanthaceae, a shrub or small tree found in the region around the Amazon and Orinoco river basins. The roots and woody stems of muira puama are popularly known for their astringent quality as a treatment for diarrhea. R. C. Wren, *Potter's New Cyclopaedia of Botanical Preparations* (1988). In addition, muira puama is included in a number of commercial formulations that purport to contain aphrodisiac activity. Clarence Meyer, *Herbal Aphrodisiacs from World Sources* (1986) (hereinafter "Meyer"). Miller has recognized that muira puama contains an unidentified resin that has a strong stimulating effect upon the human central nervous system and, assertedly, the libido. R. A. Miller, *The Magical and Ritual Use of Aphrodisiacs* (1985) (hereinafter "Miller", which is incorporated by reference herein). Astringency and sexual stimulation are believed to be the only reported activities derived from muira puama.

The muira puama root is commercially available and it usually occurs as light-brown to pink-brown hard, tough, fibrous, woody splinters. The root is odorless and has a slightly astringent taste.

The chemical constituents of muira puama are not well characterized, but it has been reported that muirapaumine, esters of benzoic acid, lupeol, and phytosterols are present. *Merck Index* (11th Ed. 1989); Auterhoff and Pankow, 301 *Arch. Pharm. (Weinheim)* 481 (1968); Auterhoff and Pankow, 302 *Arch. Pharm. (Weinheim)* 209 (1969); A. Heinz, *Drogenkunos* (1975). The root's supposed aphrodisiac activity is thought to reside in an aromatic resin of unknown composition. W. H. Lee & L. L. Lee, *Herbal Love Potions* (1991); G. W. Griffin, *Aphrodisiacs for Men* (1991) (hereinafter "Griffin"). Although it has been claimed that the active ingredient is testosterone, this claim has not been substantiated by chemical analyses. T. Fahey, *Steroid Alternative Handbook* (1993). Even if this claim were substantiated, it could not be the source of the root's purported aphrodisiac activity because oral ingestion of the root would cause any such testosterone to be rapidly degraded by the liver.

The aromatic resin is not considered to be sufficiently active when muira puama is ingested in powder form. The resin is not water soluble, therefore it cannot be extracted into water. Miller (1985); Meyer (1986); Griffin (1991). In order to prepare active quantities of muira puama, the root or bark material must be extracted with alcohol. Miller (1985) describes a typical "home use" extraction procedure consisting of mixing the powdered root with boiling vodka and straining the resulting extract before consumption. Alternatively, the resin may be extracted from the root or bark with hot isopropanol, or other alcohol, whereafter the extract is strained and evaporated. A small portion of the residue is then dissolved in the mouth to obtain the purported sexual stimulation.

Up until the present invention, muira puama has not been reported as having any use for the treatment of obesity or for increasing lean muscle mass.

There is a great need for a method of reducing body fat. Excess body fat is a known risk to good health. Obesity, or excess body fat, is an independent heart disease risk equal to that of smoking, high blood pressure, and elevated plasma lipids. The National Institutes of Health have found that obesity should be viewed as a disease. In an eight year study which included over 100,000 female nurses, the NIH found that even subjects that were slightly overweight were at an increased risk for myocardial infarction and coronary artery disease. Subjects of average weight were found to experience about 30% more heart attacks than the thinnest subjects. The risk of heart attacks for those subjects that were moderately overweight was 80% higher than that for the thin subjects. J. E. Manson et al., *New England J. Med.* 822 (1990).

Obesity is also associated with impairment of cardiac function due to an increase in the heart's mechanical workload, hypertension, stroke, diabetes, renal disease, gallbladder disease, pulmonary disease, problems in the administration of anesthesia during surgery, osteoarthritis, degenerative joint disease, gout, abnormal plasma lipid and lipoprotein concentration, menstrual irregularities, and psychological problems. S. W. Rabkin, et al., 39 *Am. J. Cardiology* 452 (1977).

Many factors may predispose a person to excessive body fat, which may be quantified as a percentage of total weight. These include: eating patterns, environment, psychological factors such as body image, and biochemical differences related to resting metabolic rate, dietary-induced thermogenesis, levels of spontaneous activity, basal temperature, levels of cellular adenosine triphosphatase, lipoprotein lipase and other enzymes, and metabolically active brown adipose tissue. K. D. Brownell & J. P. Foreyt, *Handbook of Eating Disorders* (1986); R. T. Frankel and M-W Yang, *Obesity and Weight Control* (1988).

As people age, the body fat percentage of the body increases while the important lean muscle mass decreases. K. Imamura et al., 33 *J. Gerontology* 678 (1983). The maintenance of lean muscle mass is considered extremely important as the loss of muscle strength is directly related to limited mobility and physical performance as well as to increases in the incidence of accidents suffered by the elderly. R. Goldman & M. Bockstein, *Physiology and Pathology of Aging* (1975). In addition, a number of other muscle-wasting disease conditions exist, such as late stage cancer or AIDS, in which compositions to improve lean muscle mass would be desirable.

Substances and techniques believed or reported to increase lean muscle mass and thereby decrease the percentage of body fat include alcohol, amphetamines, epinephrine, aspartates, red cell reinfusion, caffeine, protein, phosphates, oxygen-rich breathing mixtures, gelatin, lecithin, wheatgerm oil, vitamins, herbs such as ginseng, sugar, minerals, ionized air, music, hypnosis, marijuana, cocaine, anabolic steroids, and human growth hormone. F. R. Hatfield, *Ultimate Sports Nutrition* (1987). Few, if any, of these substances or techniques have been scientifically proven to be of any value, and a number, such as anabolic steroids, amphetamines, and illicit compounds, potentially have dangerous side effects.

As an example, anabolic steroids have become popular among many professional and amateur athletes. Not only have few studies documented any significant positive effects from these drugs, but they have severe adverse side effects including hirsutism, hair loss, sterility, liver disease, cancer induction, decrease in serum HDL, and development of a hostile/aggressive personality. E. E. Yesalis, *Anabolic Steroids in Sport and Exercise* (1993).

The present invention provides methods and compositions for reducing total body fat percentage while increasing lean muscle mass, and for decreasing blood cholesterol levels, by ingestion of an extract derived from muira puama. This extract does not have the severe side effects present in other known treatments.

SUMMARY OF THE INVENTION

It is a general object of the present invention to provide a method for decreasing total body fat percentage in individuals, particularly humans or other mammals.

It is another object of the present invention to provide a method for increasing lean muscle mass in individuals in need thereof, such as in cancer or acquired immune deficiency syndrome patients.

It is another object of the present invention to provide a method for decreasing one or more blood cholesterol levels in individuals.

It is a further object of the present invention to provide an extract capable of reducing total body fat percentage, increasing lean muscle mass, and/or decreasing blood cholesterol levels in individuals.

It is a further object of the present invention to provide a method for decreasing total body fat percentage, increasing lean muscle mass and/or decreasing blood cholesterol levels without the dangerous side effects of anabolic steroids.

It is another object of the present invention to provide a method of extracting a resin from muira puama and, preferably, obtaining a water washed or other solid-form extract that may be used to decrease body fat percentage, increase lean muscle mass and/or decrease blood cholesterol levels in individuals.

It is another object of the present invention to provide a method for decreasing total body fat percentage, increasing lean muscle mass and/or decreasing one or more blood cholesterol levels by treatment with muira puama resin, or a washed or other solid-form extract of muira puama, in an easily ingestible form such as in capsule form.

It is yet another object of the present invention to provide pharmaceutical compositions, preferably in unit dosage form, comprising an extract of muira puama and, especially, a washed or other solid-form extract of muira puama.

These and other objects are readily achieved by providing a method of preparing an easily ingested extract of muira puama and related pharmaceutical compositions which, when taken regularly, have the effect of decreasing body fat percentage, increasing lean muscle mass and/or decreasing blood cholesterol levels. This extract does not have the known dangerous side effects of anabolic steroids.

DETAILED DESCRIPTION OF THE INVENTION a. Extraction procedures

Muira puama root, which may be obtained commercially (for example, from herbologists or other stores that sell herbs for medicinal uses; lists of such sources may be found in Miller (1985) and in Michael Tierra, *The Way of Herbs* (1990)) in the form of chips or splinters, was used for preparation of the resins and other muira puama extracts of the present invention. In a typical extraction procedure, one pound of the root was placed in four liters of 95% ethanol for thirty days at room temperature to produce a tincture. The solution was then filtered (Whatman #1 filters; other filters of similar grade may be used) to remove root fragments. The alcohol was then allowed to slowly evaporate at room temperature for approximately one week. This extraction process produced a resin extract that had the appearance of an opaque, highly viscous, yellow-brown to black, sticky resin.

Other methods of extraction will be apparent to those skilled in the art given the present disclosure, and include distillation of the root, bark or other muira puama wood material in ethanol overnight and collection of the reflux. In addition, other alcohols, or other solvents (especially organic solvents) known to those skilled in the art, including, but not limited to ethers (e.g. ethyl ether), ketones (e.g. acetone), and esters (e.g. ethyl acetate), which are capable of extracting the muira puama resin, and which preferably are non-toxic, or at least readily removable from the product resin, may be used. The extraction solvent may be removed by alternative means, as for example by placing the extract solution in a commercial desiccator or vacuum evaporator in order to remove some or preferably all of the remaining extraction solvent.

It has been discovered by the inventor that the resin extract may be further processed into a more easily manipulatable and ingestible form by washing with water. Thus, a resin extract as prepared above was resuspended into hot water and washed by shaking for one hour. The solution was then filtered and the washed extract residue collected. The washed extract residue was thereafter allowed to dry at room temperature.

Other solutions may also be used to wash the resin extract. An important consideration is that the solution not solubilize the active component of the resin. Routine experimentation by those skilled in the art, taking into account characteristics such as polarity, will easily identify which solutions may be used to yield the desired final product. The resin may also be washed by applying heat during the washing process. The resulting solid-form extract may be dried in a desiccator or by other conventional means.

Unexpectedly, the washed residue as obtained above was a solid material which, as reported below, retained the same activity as the precursor resin extract. Moreover, as described hereinafter, the washed extract was found to have a form which, in contrast to the resin extract, could conveniently be handled and apportioned into pharmaceutically conventional dosage units, for example capsules.

The solid-form muira puama extract obtained in this manner constitutes a pharmaceutically convenient form which retains muira puama activity. The washed residue is granular and can be easily measured into required dosages, as opposed to the sticky resin form of muira puama extract. By concentrating the muira puama activity into a granular form, and encapsulating the residue into capsules, muira puama may be administered in a much more palatable manner than the resin extract. Another advantage of the granular or other solid form of muira puama extract is that it can be easily stored and shipped.

In one example of a pharmaceutical composition of the present invention, the granular muira puama extract as obtained above was mixed with ascorbic acid (which served both as a purification agent and as a binder) and encapsulated in capsules as follows. Ascorbate solution was added to the washed solid-form extract; the mixture contained an equal weight of ascorbate to extract. The mixture was stirred and the precipitate was collected by filtration. The ascorbate/washed extract precipitate had a more powder-like composition and had a lighter brown-yellow color than the original washed extract, suggesting that the ascorbate had solubilized inactive ingredients. This step should yield a higher degree of purity of muira puama activity and is a likely step to its further purification.

Other binders, stabilizers, preservatives, carriers, encapsulants, excipients or other additives (particularly solid additives) that are known to those of skill in the pharmaceutical art may be substituted for ascorbic acid. Similarly, given the present disclosure, it will be recognized that other pharmaceutical forms may be utilized to formulate compositions containing the solid-form muira puama extract of the present invention. Such forms include, for example, tablets, capsules, pills, powders, sustained release formulations, salts and the like. Likewise, non-solid-form extracts of muira puama, such as resin extracts, may be used in formulating pharmaceutical compositions within the scope of the invention, although these may be less convenient to produce or administer than the solid-form extracts.

The term "pharmaceutical composition" as used herein includes ingestible forms of the present muira puama extracts whether or not they are expressly medicinal, as for example forms designed or constituted as supplements, additives, nutrients or the like, and including bulk forms of such pharmaceutical compositions. Preferably, such pharmaceutical compositions are in a solid form, although liquid forms such as suspensions, syrups or elixirs may also be utilized. Most preferably, such compositions are in a unit dosage form (such as a tablet, capsule, pill, or apportioned powder or resin extract) containing a measured amount of the extract material per unit dose, combined with a pharmaceutically acceptable carrier. Suitable pharmaceutical additives and formulations are described in, for example, E. W. Martin, *Remington's Pharmaceutical Sciences*.

The amount of muira puama extract active ingredient in such pharmaceutical compositions may be adjusted to achieve an effective dosage unit. Preferably, the dosage units (e.g. capsule, pill, or other measured portion) are formulated so as to allow the convenient administration of an amount of muira puama active ingredient derived from about 0.025 grams to about 0.6 grams, more preferably about 0.075 grams to about 0.3 grams, and most preferably about 0.15 grams, of starting muira puama wood material per kilogram of subject weight per day. Thus, assuming a typical subject weight of 75 kilograms, each dosage unit may contain an amount of muira puama active ingredient derived from about 5.6 grams to about 22.5 grams, or preferably about 11.25 grams, of muira puama wood material, or some convenient measured fraction thereof. Alternatively, the amount of active ingredient is based directly on the weight of muira puama extract in the dosage unit, in which case the weight amount of extract will depend on the purity of the extract (e.g., a resin or washed resin form of the extract). In this case, each dosage unit may contain between about 10 mg and about 500 mg of muira puama extract, or some convenient fraction thereof, as measured based on the amount of muira puama active ingredient contained in the washed or crude resin form of the extract. More preferably, each unit dose will contain between about 25 mg and about 250 mg of the extract, and most preferably between about 50 mg and about 100 mg (again based on the concentration of active ingredient in the resin form of the extract), or some convenient fraction thereof. Smaller actual weight amounts of muira puama extract, or isolated or synthetic forms of the active ingredient, may be used in a unit dose to the extent the muira puama active ingredient is further purified, and are the equivalent of the resin-based dosages set forth above. Those skilled in the art will be able to ascertain the equivalent amounts to be used in these cases in order to achieve the functions and results taught herein.

Preferably, such compositions will be packaged in kits containing dosage units or other measured portions of the muira puama extract and instructions for the use of the composition in decreasing body fat, increasing muscle mass and/or lowering blood cholesterol levels. As explained hereinafter, suitable instructions for these purposes will specify that the composition be ingested in a repeated series of doses according to a regular schedule (preferably daily or twice daily) over an extended period (preferably at least one month, and more preferably at least three months or until a desired level of fat loss, lean mass gain or cholesterol lowering have been achieved).

b. Therapeutic Activity

EXAMPLE 1

Animal Studies of Efficacy of Muira Puama Extract

In this study, it was demonstrated that an extract of muira puama used according to the therapeutic method of the present invention was effective in reducing both fat gain and cholesterol levels in animal subjects.

Twenty-four male Wistar rats (mean weight 230±10 grams) were randomly divided into four groups of six rats each. Two of the groups were fed ad libitum during the course of the study, and the other two groups were allowed a restricted food intake of 15 grams of chow per day. All groups were fed a reduced-oil Purina rat chow that, upon supplementation with 200 µL/day of sesame oil as explained below, was otherwise equivalent in composition and food value to standard Purina rat chow.

One group of rats from each of the ad libitum and the restricted-intake populations received a daily oral administration of muira puama extract in 200 µL sesame oil, and the remaining two groups received 200 µL/day of sesame oil alone as a control. The muira puama/oil composition was prepared by suspending the resin extract obtained from 84 grams of muira puama root, prepared by extraction from native muira puama as described in the foregoing detailed description, in 450 mL of light sesame oil. The 200 µL/day dose of the muira puama/oil composition corresponded to the amount of resin extract obtained from approximately 0.15 grams of muira puama root per kilogram of body weight per day, which is a preferred human dosage level. Administration was achieved in each case using a feeding tube.

After approximately 3–4 weeks, rat body weights and perirenal pad weights were determined, and blood chemistry was analyzed. As expected, the restricted food intake animals showed lower body weight gains than the ad libitum fed animals (~50 gram weight gain vs. ~160 gram weight gain). In the ad libitum groups, both the muira puama treated and the control animals showed virtually the same weight gain (161 grams vs. 162 grams). In the calorie restricted animals, the muira puama treated animals gained slightly more weight than the control animals, but the difference was not statistically significant (55±19 grams vs. 46±11 grams).

In the absence of a different total weight gain, however, differences were found in the fat gain of the animals. In the ad libitum groups, the control animals had perirenal fat pad weights of 1.25±0.26 grams while the muira puama treated animals had pad weights of 0.96±0.24 grams. This difference was significant a p value of 0.05 or better. The calorie restricted animals did not show a statistically significant difference, the pad weight being approximately 0.45 grams for both groups in this population.

These results demonstrate that, in ad libitum fed animals showing normal overall weight gain, the muira puama composition had the effect of decreasing the deposition of fat and, correspondingly, shifting the overall weight gain toward lean mass gain.

Significantly, blood chemistry analysis showed substantial reductions in total cholesterol levels in the muira puama treated animals. This beneficial effect was seen in both the ad libitum and the restricted intake animal groups. Thus, treatment with the muira puama composition reduced the total cholesterol level in the ad libitum fed animals by about 25% (from 48±11 to 36±6), and in the restricted intake animals by about 15% (from 48±12 to 41±6). These decreases were significant at a p=0.005 level or better. In all cases the cholesterol/HDL ratios were not altered.

Serum triglyceride levels were also altered by the muira puama treatment. In the ad libitum fed animals that received muira puama, triglycerides increased by about 65% (from 390±153 to 647±260; p=0.05). In the restricted intake group, muira puama treatment also showed a trend toward increased triglycerides (425±311 to 529±219; p=0.2–0.3), although the results were not highly significant. These increased serum triglyceride levels, particularly in the ad libitum group, suggest that muira puama causes a beneficial mobilization of fat in the treated animals.

Further blood chemistry analyses of blood urea nitrogen (BUN) and creatinine levels showed only a minimal effect of muira puama treatment, which is consistent with the preservation or anabolism of muscle in the treated animals.

EXAMPLE 2

Human Studies of Efficacy of Muira Puama Extract

The muira puama composition of the present invention, prepared from a resin extract as described above, was administered to a healthy male subject, age 45 years, who had maintained a stable (within two pounds) weight of 105 pounds over more than ten years. Before treatment, the subject was normotensive and his baseline blood chemistries were normal, except for a slightly elevated cholesterol level with an HDL of approximately 50. Liver function tests were normal. The subject's body fat percentage was 18%, measured using the girth measurement method. The subject's diet and exercise pattern (walking two to three miles per day) did not change significantly throughout the study.

The subject ingested the muira puama extract (resin form) in a dose of 50 to 100 mg twice a day. After three months, the subject's weight increased by fifteen pounds. The subject's blood chemistries remained normal, and the cholesterol level was slightly decreased. The subject's HDL level rose from 50 to 75. Increased HDL levels are believed to be beneficial, V. Manninen et al., 260 JAMA 641 (1988), therefore this increase suggests an improvement in the subject's health status. The subject's body fat percentage, as measured using the girth measurement method, was 13%. This 5% decrease, accompanied by a fifteen pound weight gain, indicates that the additional weight had been preferentially shifted toward lean muscle mass.

Following this initial study phase, the subject then received the washed muira puama extract, as described above, formulated into capsules using ascorbic acid as a binder, at a dosage of 50 mg twice a day. Dietary and exercise patterns remained constant. After three months, the subject experienced an additional ten pound weight gain. The subject's body fat remained at 13% despite the weight gain. Blood chemistries remained constant, and the subject's HDL level remained at approximately 75.

The subject then discontinued treatment for three months. Total body weight after the three months was within two pounds of the weight measured before the treatment was discontinued. Nevertheless, the subject's body fat percentage increased to 18%, a 5% increase following discontinuation of the treatment.

The subject then reinstituted treatment, ingesting the washed extract in capsules at a dose of 50 mg per day. Within one month, the subject lost three to five pounds of body weight, and the subject's body fat percentage returned to 13%. Three months later (after four months of reinstituted treatment), the subject's weight returned to the value it was four months previously (i.e., the weight before reinstituting treatment), while the body fat percentage remained at 13%.

Subjectively, the subject's physician noted that the subject's appearance seemed less thin and more muscular than before treatment with the muira puama extract.

The subject did not experience any alterations in facial or body hair, exacerbation of acne, or alterations in liver function tests, symptoms commonly experienced after treatment with anabolic steroids. Although the exact mechanism by which muira puama decreases body fat is unknown at this time, these results most likely indicate that the mechanism is not the same as that used by anabolic steroids.

The foregoing entailed description represents the best mode presently known to the inventor of practicing the invention, and is not intended to limit the scope of the present invention, which is set forth in the following claims. Likewise, those skilled in the art, given the present disclosure, will recognize that equivalent methods and materials may also be used in practicing the invention. It is contemplated that such equivalents are also within the scope of the present invention.

I claim:

1. A solid-form extract of muira puama produced by the steps of (1) extracting a muira puama resin from muira puama wood material by mixing said wood material with an extraction solvent capable of solubilizing said resin, (2) removing non-solubilized wood materials from the extraction solvent mixture, (3) removing said extraction solvent to yield a muira puama resin extract, (4) washing said resin extract in a second solvent in which said resin is substantially insoluble, and (5) drying said washed resin extract to yield a solid-form extract of muira puama.

2. A solid-form extract of muira puama according to claim 1 wherein said extraction solvent comprises an alcohol solvent.

3. A solid-form extract of muira puama according to claim 1 wherein said second washing solvent comprises water.

4. A pharmaceutical composition comprising the solid-form muira puama extract of claim 1 and a pharmaceutically acceptable carrier.

5. The pharmaceutical composition of claim 4, wherein the composition is in a unit dosage form containing from about 10 to about 500 mg of said solid-form muira puama extract per unit dose.

6. A pharmaceutical composition comprising, in combination with a pharmaceutically acceptable carrier, an extract of muira puama produced by the steps of (1) extracting a muira puama resin from muira puama wood material by mixing said wood material with an extraction solvent capable of solubilizing said resin, (2) removing non-solubilized wood materials from the extraction solvent mixture, and (3) removing said extraction solvent to yield a muira puama resin extract.

7. A pharmaceutical composition for oral ingestion comprising a measured portion of an extract of muira puama and a pharmaceutically acceptable carrier.

8. The pharmaceutical composition of claim 7, wherein the composition is a solid-form composition selected from the group consisting of capsules, tablets, pills or powder form compositions.

9. The pharmaceutical composition of claim 7 further comprising a solid binder as an additive.

10. The pharmaceutical composition of claim 7, wherein the composition is in a unit dosage form containing from about 10 to about 500 mg of muira puama extract per unit dose.

11. A method of decreasing body fat percentage in a mammalian subject comprising administering to the subject a repeated series of doses of the solid-form muira puama extract of claim 1.

12. A method of decreasing body fat percentage in a mammalian subject comprising administering to the subject a repeated series of doses of the pharmaceutical composition of claim 7.

13. A method of increasing lean muscle mass in a mammalian subject comprising administering to the subject a repeated series of doses of the solid-form muira puama extract of claim 1.

14. A method of increasing lean muscle mass in a mammalian subject comprising administering to the subject a repeated series of doses of the pharmaceutical composition of claim 7.

15. A method of lowering the cholesterol level of a mammalian subject comprising administering to the subject a repeated series of doses of the solid-form muira puama extract of claim 1.

16. A method of lowering the cholesterol level of a mammalian subject comprising administering to the subject a repeated series of doses of the pharmaceutical composition of claim 7.

17. A kit for use in decreasing body fat percentage, increasing lean muscle mass or lowering the cholesterol level of a mammalian subject, comprising (1) a measured portion of a solid-form muira puama extract and (2) instructions directing the ingestion by the subject of said extract in a repeated series of doses over a period of time sufficient to decrease body fat, increase muscle mass or lower cholesterol levels.

18. The kit according to claim 17 wherein said muira puama extract is in a unit dosage form.

\* \* \* \* \*